United States Patent [19]

Henig

[11] Patent Number: 4,570,635

[45] Date of Patent: Feb. 18, 1986

[54] ELECTRICAL DEVICE FOR ALLEVIATING EARACHE PAIN

[76] Inventor: Ronald Henig, 259 Maxwell St., Downsview, Ontario, Canada, M3H 5C1

[21] Appl. No.: 569,724

[22] Filed: Jan. 10, 1984

[51] Int. Cl.4 .............................................. A61F 7/12
[52] U.S. Cl. ................................... 128/380; 128/401; 219/211
[58] Field of Search ............... 128/380, 385, 387, 401, 128/402, 403, 384; 2/209, 423; 219/211

[56] References Cited

U.S. PATENT DOCUMENTS

| | | | |
|---|---|---|---|
| 915,824 | 3/1909 | Branaman | 128/380 |
| 3,407,818 | 10/1968 | Costanzo | 219/211 X |
| 3,796,855 | 3/1974 | Brown et al. | 219/211 |
| 3,885,403 | 5/1975 | Spencer | 128/403 X |
| 4,034,787 | 7/1977 | Ellis | 128/401 |

Primary Examiner—Anton O. Oechsle

[57] ABSTRACT

The present invention provides a headband provided with a pair of electrically heated ear plugs for alleviating earache pain caused by middle and inner ear infection. The ear plugs themselves each comprise a heat generating member surrounded by a soft and malleable material for both conducting heat from the heat generating member to region of the earache pain and substantially conforming to the inner surface of the ear.

5 Claims, 3 Drawing Figures

ELECTRICAL DEVICE FOR ALLEVIATING EARACHE PAIN

FIELD OF THE INVENTION

The present invention relates to a device having electrically heated ear plugs for alleviating earache pain caused by middle and inner ear infection.

BACKGROUND OF THE INVENTION

As most people will appreciate inner ear infections can be extremely painful particularly where young children are concerned. The standard method of treating inner earache pain is to plug the ear with cotton balls and the like to produce a heat buildup within the ear for reducing the earache pain.

Other arrangements have been devised for producing earache relieving heat within the ear. For example, U.S. Pat. No. 915,824 describes an electrical head cap including a pair of ear bobs which form the terminals of the battery to warm the inner surface of the ear. However, according to this prior art arrangement the ear bobs are in the form of elongated projections which are both uncomfortable and dangerous for fitting inside of an ear.

A further ear warming device is described in U.S. Pat. No. 3,796,855. This particular ear warming device does not suffer from the potentially dangerous features described above in that it does not fit into the ear. However, at the same time, because it does not fit into the ear, it does not provide a direct contact for transferring heat immediately to the source of the pain at the middle and inner ear.

SUMMARY OF THE PRESENT INVENTION

The present invention provides a device adapted to safely alleviate earache pain by applying heat directly to the ear inner surface, and in particular the ear canal of an ear. The device comprises a headband, a pair of ear plugs extending inwardly from opposing sides of the headband with each of the ear plugs comprising a heat generating member surrounded by a heat conductive material which is soft and malleable for safely fitting into the ear and for substantially conforming to and warming the ear canal by conducting heat from the heat generating member to the source of the pain. The device further includes an electrical power source which, according to a preferred embodiment of the invention, is carried directly with the headband for operating the heat generating members of the ear plugs.

BRIEF DESCRIPTION OF THE DRAWINGS

The above as well as other advantages and features of the present invention will be described in greater detail according to the preferred embodiments of the present invention in which.

DETAILED DESCRIPTION ACCORDING TO THE PREFERRED EMBODIMENTS

Figure 1:
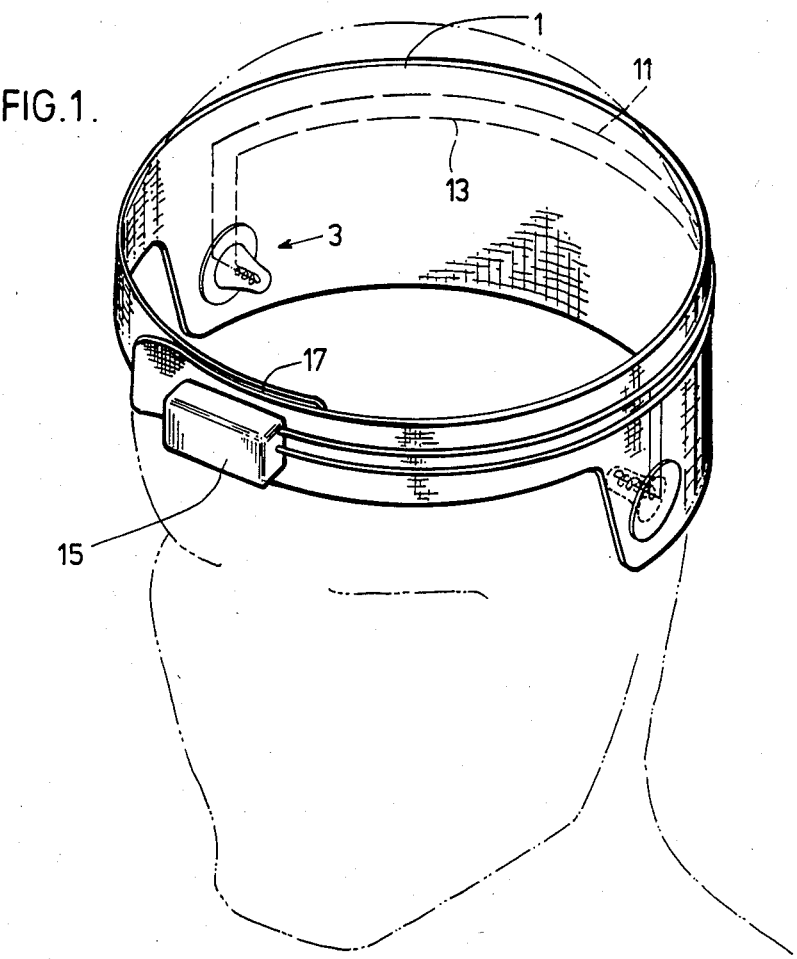
FIG. 1 is a perspective view looking down on a earache pain relieving device according to a preferred embodiment of the present invention.

FIG. 1 shows the overall device comprising a headband 1 which is made from a soft cloth material or the like for comfortably and snugly wearing around one's head and provided with a pair of ear plugs 3 extending inwardly from opposing sides of the headband. The headband itself is adjustable to different head sizes and includes a VELCRO fastener system 17 although other adjustable fasteners could also be used mounted directly to the outer surface of the headband is a battery compartment 15 for receiving a battery 14, shown in FIG. 2.

Figure 2:
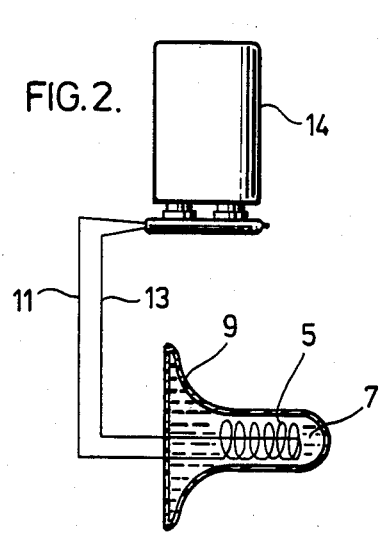
FIG. 2 is a schematic of the electrical wiring of one of the ear plugs of the device shown in FIG. 1.

A pair of positive and negative leads 11 and 13 run from battery 14 to each ear plug as best shown in FIG. 2. The battery itself in this embodiment, consists of a standard 9 Volt power cell with the ear plug being provided with an internal coil 5 which is adapted to transform the current from battery 14 into a safe level of heat energy for warming the inner surface of the ear. This coil 5 is emersed within a gel filled plug portion 7. This plug portion totally surrounds the heating coil to provide a safe and comfortable fit within the ear in that the plug portion with its gel fill is designed to fit into and conform to the surface of the ear canal. Furthermore the gel fill is heat conductive to conduct the heat from coil 5 directly to the ear canal surface and at the same time is soft and malleable for fitting to different shapes and sizes of ear canals as shown in FIG. 3.

Futhermore since the plug shapes to and contacts the ear canal it provides a substantial heat transfer surface around the ear plug with the ear canal which would not be the case if the ear plug did not shape to the ear canal and only made limited, if any contact. The ear plug further includes an outer flexible portion 9 which covers the ear opening to both assist in the fitting of the ear plug and to trap the heat in the ear.

The embodiment described above is totally portable in that the power source for the ear plugs is carried directly with the headband. The device could however be operated from an AC power source with a step-down transformer for reducing the heat energy produced at the ear plug to a safe level within the ear. The device could further be arranged to accommodate both the portable and the external power source.

Figure 3:
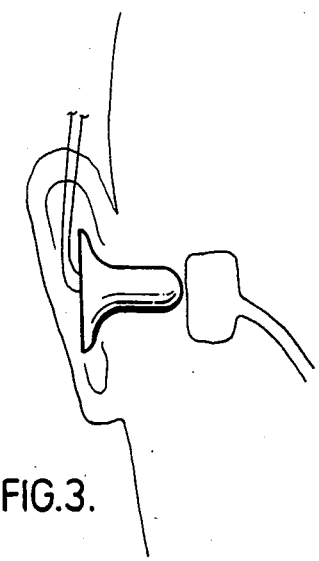
FIG. 3 is a view showing the fitting of the ear plug shown in FIG. 2, into an earache relieving position within an ear.

As will be seen in FIG. 3 the earache pain relieving device of the present invention directs heat immediately to the source of most earache problems, namely the middle and inner ear where ear infections often occur. Furthermore the heat is directed to this region by a plug arrangement which will safely and comfortably fit to different shapes and sizes of ears so that the device can be used by children and grownups alike. However, although various preferred embodiments of the present invention have been described herein in detail, it will be appreciated by those skilled in the art, that variations may be made thereto without departing from the spirit of the invention or the scope of the appended claims.

The embodiments of the invention in which an exclusive property or privilege is claimed are defined as follows:

1. A device to alleviate earache pain, said device comprising a headband, a pair of ear plugs extending inwardly from opposing sides of said headband for fitting into an ear canal, said ear plugs each comprising a heat generating member surrounded by a heat conductive material which is soft and malleable for both substantially conforming to and warming the ear canal by heat from said heat generating member, and an electrical power source for operating the heat generating members of the ear plugs, each ear plug comprising a heating coil, a gel filled portion around said heating coil, and an outer flexible ear opening portion for maintaining heat from said heating coil within the ear.

2. A device is claimed in claim 1 wherein said power source comprises a 9 Volt battery carried within a battery compartment mounted to said headband.

3. A device as claimed in claim 2 wherein said headband is adjustable to different head sizes.

4. A device as claimed in claim 3 including a Velcro ™ fastener for said headband.

5. A device as claimed in claim 3 wherein said headband comprises a softened cloth material for fitting comfortably and snugly in position.

* * * * *